United States Patent
Arzate et al.

(10) Patent No.: US 6,412,337 B1
(45) Date of Patent: Jul. 2, 2002

(54) APPARATUS AND METHOD FOR MEASURING THE RHEOLOGICAL PROPERTIES OF A POWER LAW FLUID

(75) Inventors: Alfa Arzate, Montreal; François Bertrand, Ville St-Laurent; Olivier Reglat, Montreal; Philippe Tanguy, Ville St-Laurent, all of (CA)

(73) Assignee: Polyvalor S.E.C., Montreal (CA)

( * ) Notice: Subject to any disclaimer, the term of this patent is extended or adjusted under 35 U.S.C. 154(b) by 0 days.

(21) Appl. No.: 09/493,414

(22) Filed: Jan. 28, 2000

(51) Int. Cl.$^7$ .............................................. G01N 11/04
(52) U.S. Cl. ................... 73/54.09; 73/54.02; 73/54.04; 73/54.05; 73/54.06
(58) Field of Search ............................ 73/54.02, 54.04, 73/54.05, 54.06, 54.09

(56) References Cited

U.S. PATENT DOCUMENTS

| | | | |
|---|---|---|---|
| 3,468,158 A | * 9/1969 | Chien ........................ 73/54.05 |
| 3,528,281 A | * 9/1970 | Cowan ....................... 73/54.09 |
| 4,067,230 A | 1/1978 | Ball |
| 4,350,285 A | * 9/1982 | Holben ................. 73/54.06 X |
| 4,612,800 A | 9/1986 | Erian |
| 4,644,781 A | * 2/1987 | Mon ........................ 73/54.05 |
| 4,680,957 A | 7/1987 | Dodd ........................ 73/54.04 |
| 4,726,219 A | 2/1988 | Pearson et al. ............ 73/54.04 |
| 4,750,351 A | 6/1988 | Ball |
| 5,014,545 A | * 5/1991 | Rao ........................... 73/54.09 |
| 5,078,007 A | 1/1992 | Tadros |
| 5,095,755 A | 3/1992 | Peterson |
| 5,315,863 A | 5/1994 | Cowper ..................... 73/54.09 |
| 5,347,852 A | 9/1994 | Mode ........................ 73/54.04 |
| 5,359,881 A | 11/1994 | Kalotay |
| 5,583,284 A | * 12/1996 | Martin et al. .............. 73/54.09 |
| 5,877,409 A | * 3/1999 | Girling ...................... 73/54.06 |

* cited by examiner

Primary Examiner—Daniel S. Larkin
(74) Attorney, Agent, or Firm—Bourque & Associates, PA

(57) ABSTRACT

The apparatus (10) is used for determining the consistency index (k) and the power law index (n) of a Newtonian fluid or non-Newtonian power law fluid. A method is also disclosed. Accordingly, the fluid flows in a laminar manner through a first (12) and a second static mixer (14) successively connected together by means of an intermediary pipe (18). A first pressure differential ($\Delta P_1$) corresponding to a pressure drop of the fluid through the first static mixer (12) is measured. Similarly, a second pressure differential ($\Delta P_2$) corresponding to a pressure drop of the fluid through the second static mixer (14) is measured. Finally, the consistency index (k) and the power law index (n) are calculated using the Metzner and Otto concept generalized to static mixers. The apparent viscosity may also be calculated. This invention may be mounted directly on a main supply pipe (16) and allows the rheological properties of the fluid to be known in real time. It also improves the mixing of the fluid and maintains its homogeneity.

22 Claims, 4 Drawing Sheets

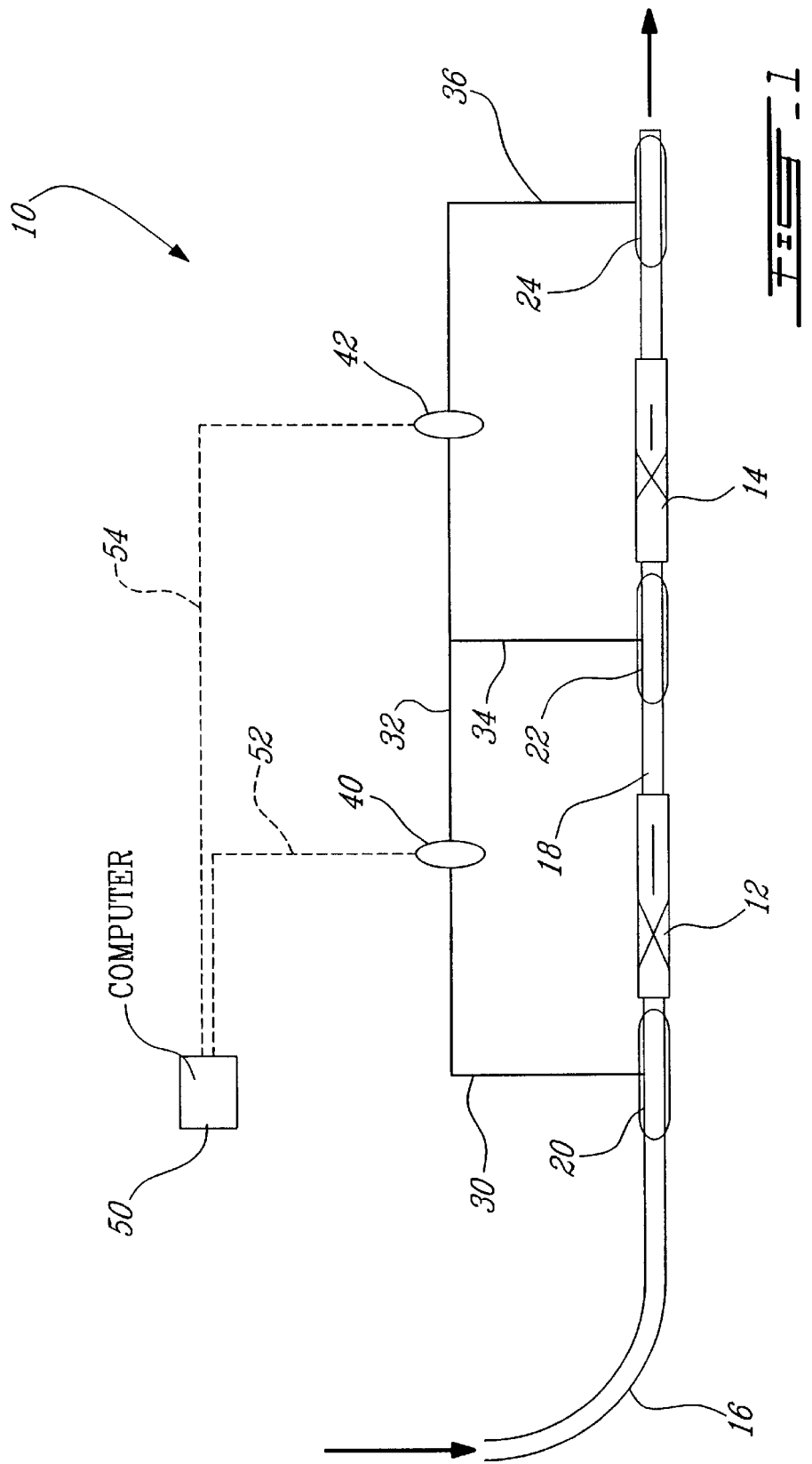

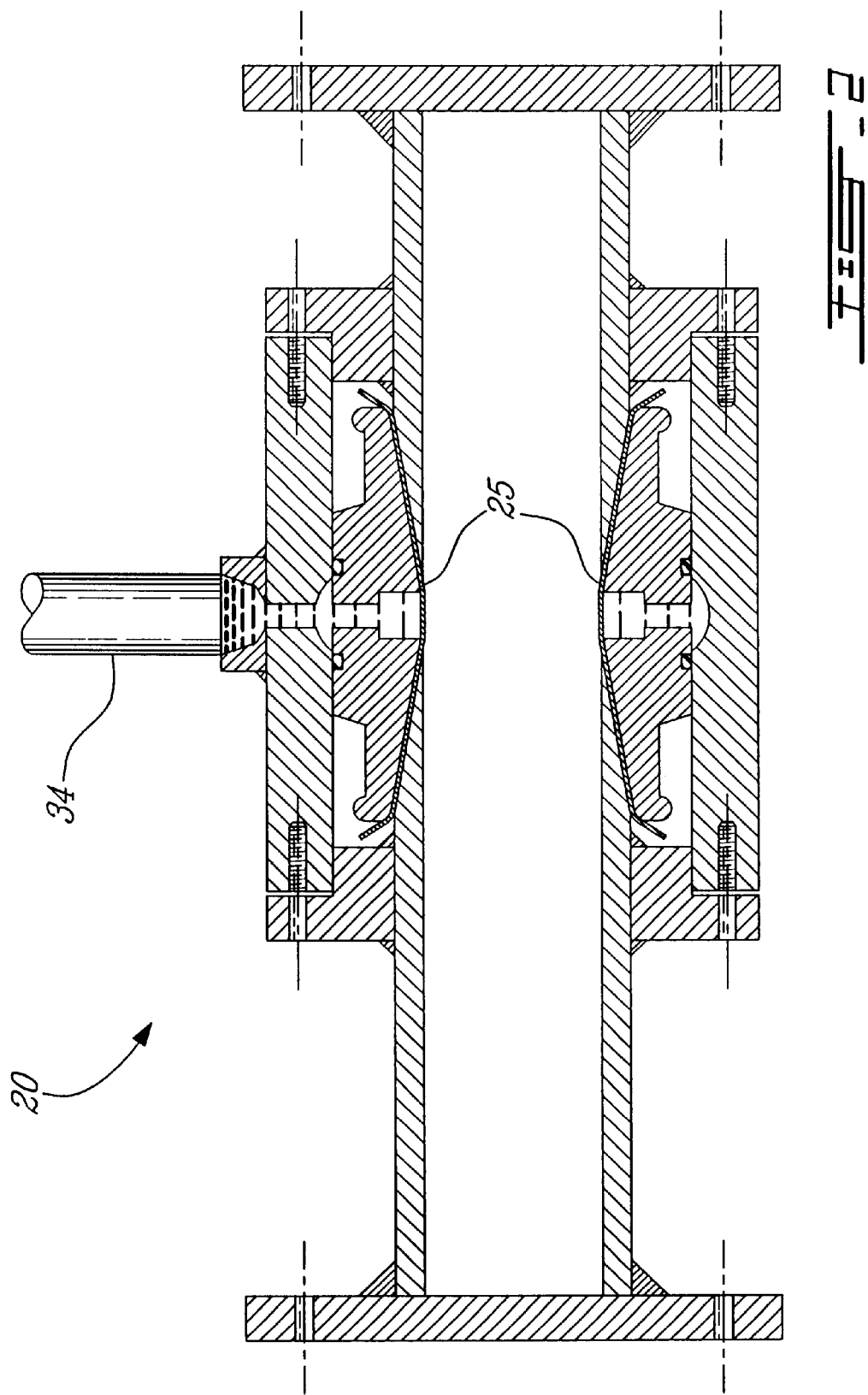

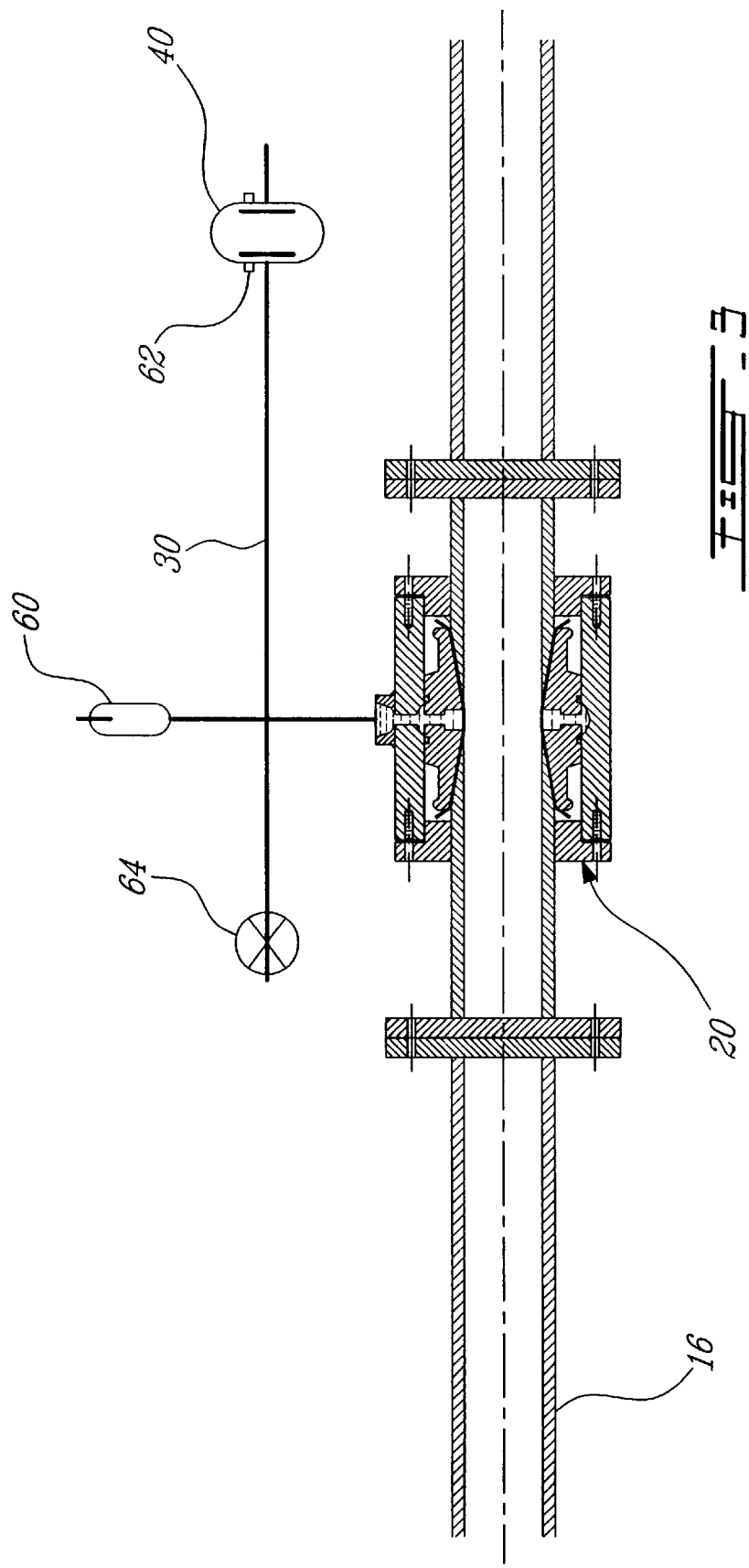

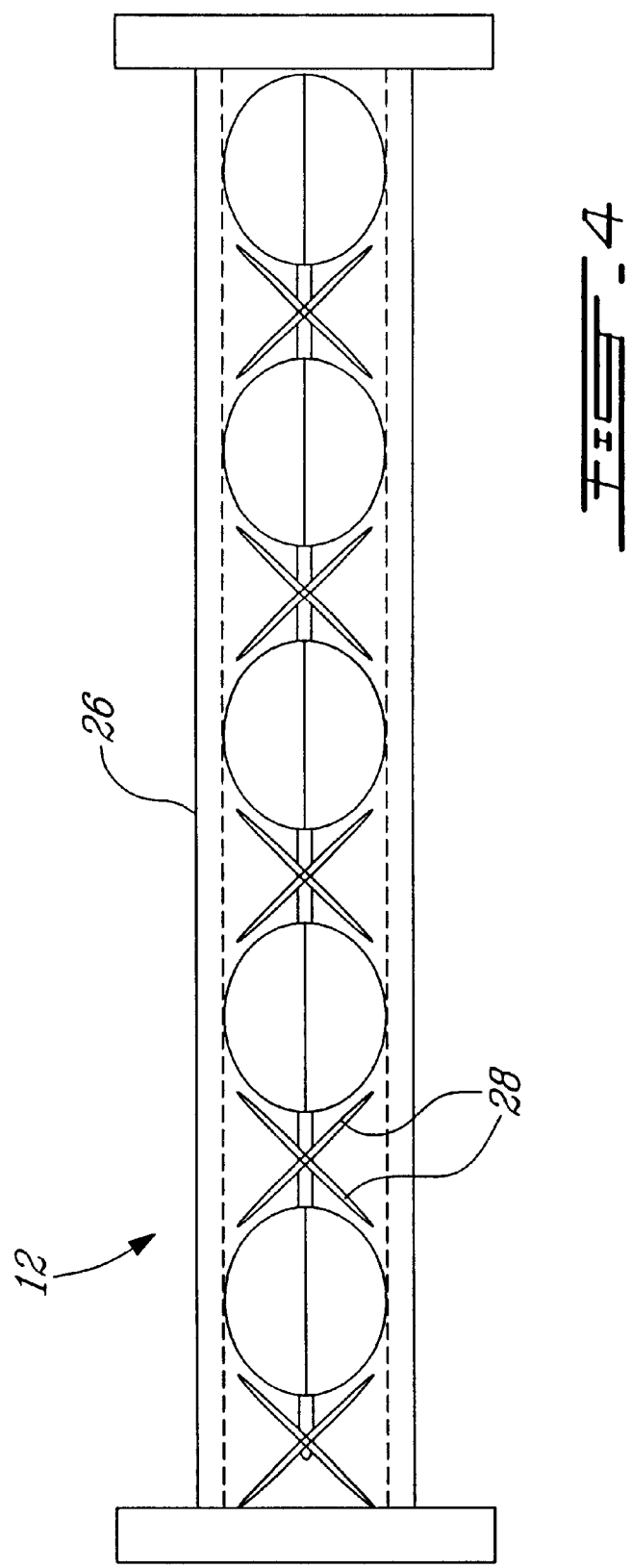

APPARATUS AND METHOD FOR MEASURING THE RHEOLOGICAL PROPERTIES OF A POWER LAW FLUID

The invention is concerned with an apparatus and a method for measuring the Theological properties of a Newtonian or a non-Newtonian fluid exhibiting a power law behavior in a tube and which is flowing in a laminar manner. This invention allows the consistency index (k) and the power law index (n) to be known in real time. It also improves the mixing of the fluid and maintains its homogeneity.

In many industrial processes, the quality of final products depends on several key physical properties, such as density, temperature, pressure, flow rate, pH, solid concentration, flow characteristics and others. These physical properties and their evolution need to be monitored and kept within given limits so as to maintain or even enhance the quality and constancy of the final products. Yet, knowing the physical properties in real time is essential in a fully automated process to provide an adequate feedback to the control system in which the target values of the parameters have been programmed. If necessary, the control system changes the amounts of ingredients or adjusts the various settings while the process is underway.

Among the physical parameters to monitor, the ones related to the flow characteristics of the materials are particularly important in a wide range of applications. Knowing the flow characteristics is the prime interest of the science of rheology. One of the key parameters in rheology is the viscosity, which may be roughly defined as the resistance to the flow of adjacent layers of a fluid in motion. All fluids exhibit viscosity to some degree. This parameter thus signals how a fluid flows under the influence of an external force or gravity. Viscosity is usually expressed in terms of Pascal-seconds or the equivalent.

Rheology characterizes fluids in two main categories, namely Newtonian fluids and non-Newtonian fluids. Sir Isaac Newton had long ago established that there is a direct linear relationship in some fluids between the shear stress ($\tau$) necessary for obtaining the movement and the effective shear rate ($\gamma$). The apparent viscosity (72) of these fluids is not affected by the shear rate ($\gamma$) and remains constant. The fluids that show this flow behavior are classified as Newtonian fluids. The ones that cannot be characterized by this kind of flow behavior are classified as non-Newtonian fluids. Some non-Newtonian fluids may have for instance a dilatant flow behavior, also referred to as a shear-thickening behavior, which is characterized by an increase in viscosity as the shear rate increases. Others may have a plastic flow behavior, also referred to as a shear-thinning behavior, characterized by a decrease in viscosity as the shear rate increases.

A power fluid is defined as any shear-thinning fluid or shear-thickening fluid having a linear relationship between $\log(\eta)$ and $(\log(k)+(n-1) \log(\gamma))$, wherein $\gamma$ is the shear rate and $\eta$ is the apparent viscosity. k and n are two rheological parameters, namely the consistency index (k) and the power law index (n). Newtonian fluids are also power law fluids since their flow behavior is a particular case of this relationship. Non-Newtonian fluids are far more complicated since they can behave as a power law fluid in one environment and not in another. For instance, it is possible to have a non-Newtonian fluid that exhibits a power law behavior when flowing in a particular pipe and not when submitted to a high shear rate, for example $10^4 s^{-1}$ or more.

The apparent viscosity ($\eta$) of non-Newtonian fluids depends on the effective shear rate ($\gamma$) when the measure is taken. The value of apparent viscosity ($\eta$) is thus provided with an indication of the effective shear rate ($\gamma$) or where the measure is taken. For instance, the apparent viscosity ($\eta$) is not the same in a pipe and in a static mixer. A non-Newtonian power law fluid is more conveniently characterized by the values of the consistency index (k) and the power law index (n). The apparent viscosity ($\eta$) can be calculated using the equation $\log(\eta)=\log(k)+(n-1) \log(\gamma)$. Newtonian fluids have a power law index (n) equal to 1 and the value of the consistency index (k) gives the apparent viscosity ($\eta$), called the dynamic viscosity ($\mu$) for these fluids.

Although apparatuses dedicated to rheological measurements in real time are found in the prior art, they cannot always be used with all fluids, particularly with fluids containing a high concentration of solid particles and which are likely to create sedimentation problems. For instance, paper coating fluid compositions generally comprise solid particles whose size is generally between 0,1 and 5.0 $\mu$m. These particles are known to accumulate or migrate from walls in conventional viscometers, and thus require frequent cleaning.

In U.S. Pat. No. 4,680,957 issued on Jul. 21, 1987 and invented by Stephen C. Dodd, the consistency of a non-Newtonian fluid flowing in a laminar manner is directly calculated from a power-law model equation using a free-line pressure loss measurement. However, a shortcoming of this invention is that the pressure loss is not significant unless highly viscous and homogeneous fluids are used. If the fluid does not have a high viscosity, the value of pressure drop would not be significant enough.

The present invention provides an apparatus and a method which allows one to make accurate real time measurements of the rheological properties of a Newtonian or a non-Newtonian fluid exhibiting a power law behavior in a tube and which is flowing in a laminar manner.

More particularly, there is provided a method for determining the consistency index (k) and the power law index (n) of a fluid exhibiting a power law behavior when flowing through a pipe having an internal diameter (D), the fluid flowing in the pipe with a mean flow velocity (V), the method being characterized in that it comprises the steps of:

passing the fluid in a first and a second static mixer through which the fluid flows in a laminar manner, the first and the second static mixer being in fluid communication with each other and being non-identical, the first static mixer having predetermined geometrical constants $K_{S1}$ and $K_{P1}$ and the second static mixer having predetermined geometrical constants $K_{S2}$ and $K_{P2}$;

measuring a first pressure differential ($\Delta P_1$) corresponding to a pressure drop of the fluid through the first static mixer;

measuring a second pressure differential ($\Delta P_2$) corresponding to a pressure drop of the fluid through the second static mixer; and calculating the consistency index (k) and the power law index (n) using the first and second pressure differentials ($\Delta P_1$, $\Delta P_2$), the mean flow velocity (V), and the geometrical constants $K_{S1}$, $K_{P1}$, $K_{S2}$ and $K_{P2}$ according to Metzner and Otto concept generalized to static mixers.

The present invention also provides an apparatus for measuring the consistency index (k) and the power law index (n) of a fluid exhibiting a power law behavior when flowing through a pipe having a given diameter (D) and with a mean flow velocity (V), the apparatus being characterized in that it comprises:

a first static mixer having an inlet and an outlet, the inlet of the first static mixer being connected to the pipe, the first static mixer having predetermined geometrical constants $K_{S1}$ and $K_{P1}$;

a second static mixer having an inlet, an outlet and being non-identical to the first static mixer, the outlet of the second static mixer being connected to the pipe, the second static mixer having predetermined geometrical constants $K_{S2}$ and $K_{P2}$;

an intermediary pipe connected between the outlet of the first static mixer and the inlet of the second static mixer;

first means for measuring a first pressure differential ($\Delta P_1$) corresponding to a pressure drop of a laminar flow of the fluid through the first static mixer;

second means for measuring a second pressure differential ($\Delta P_2$) corresponding to a pressure drop of the laminar flow of fluid through the second static mixer; and third means for calculating the consistency index (k) and the power law index (n) according to Metzner and Otto concept generalized to static mixers.

The present invention also relates to an apparatus for measuring the consistency index (k) and the power law index (n) of a fluid exhibiting a power law behavior when flowing through a pipe, the apparatus being characterized in that it comprises:

a first static mixer having an inlet and an outlet, the inlet of the first static mixer being connected to the pipe, the first static mixer having predetermined geometrical constants $K_{S1}$, and $K_{P1}$;

a second static mixer having an inlet and an outlet, the outlet of the second static mixer being connected to the pipe, the second static mixer having predetermined geometrical constants $K_{S2}$ and $K_{P2}$;

an intermediary pipe mounted between the outlet of the first static mixer and the inlet of the second static mixer;

a first pressure cell mounted on the pipe before the inlet of the first static mixer;

a second pressure cell mounted on the intermediary pipe;

a third pressure cell mounted on the pipe after the outlet of the second static mixer;

a first differential pressure transducer connected between the first and the second pressure cell, the first differential pressure transducer having an output terminal for a first pressure differential signal ($\Delta P_1$) indicative of a pressure drop of the fluid through the first static mixer;

a second differential pressure transducer connected between the second and the third pressure cell, the second differential pressure transducer having an output terminal for a second pressure differential signal ($\Delta P_2$) indicative of a pressure drop of the fluid through the second static mixer; and a computer having a subroutine in which the consistency index (k) and the power law index (n) are calculated according to Metzner and Otto concept generalized to static mixers.

The present invention can be used with a Newtonian fluid or a non-Newtonian power law fluid and does not involve the use of rotating parts lying in the path of the fluid and on which sedimentation may occur. If desired, determination of the rheological properties of the fluid can be made by providing the apparatus directly on the main pipe through which the fluid flows between stages of a process, for instance between the production of a paper coating fluid and the device used for applying the coating fluid as a film over a paper web. Another important advantage is that the two static mixers used in the present invention improve the homogeneity of the fluid in terms of fluid segregation, particle sedimentation, and temperature uniformity.

The present invention will be better understood from the following description and appended figures in which:

FIG. 1 is a schematic view of an apparatus according to a preferred embodiment of the present invention;

FIG. 2 is a cross-sectional view of an example of a pressure measuring cell;

FIG. 3 shows the measuring circuit of the pressure measuring cell of FIG. 2; and FIG. 4 is a schematic representation of the interior of a static mixer.

OVERVIEW

The basic principle of the present invention is that the consistency index (k) and the power law index (n), describing the rheological behavior of a power law fluid are calculated from pressure drop measurements taken between the inlet and the outlet of two non-identical and successive static mixers. The method involves the application of the Metzner and Otto concept generalized to static mixers, which enables one to relate the effective shear rate to the pressure drop in the case of a laminar fluid flow. The method relies on the determination of the geometric constants $K_S$ and $K_P$ specific to each static mixer. The geometric constants $K_S$ and $K_P$ depend on the geometry of each static mixer and are obtained through a prior calibration procedure from a power correlation between a Newtonian model fluid and a non-Newtonian power law model fluid. These constants are not dependent on the mean flow velocity (V), provided that the regime remains laminar.

It should be noted that the expression "power law fluid" means a fluid exhibiting a power law behavior when flowing in the pipe to which is connected an apparatus according to the present invention. Also, the term "pipe" also includes any tube, line, or conduit through which the fluid may be suitably carried. Although the term "pipe" mainly refers to a main supply pipe through which the entire amount of the fluid flows, one can use the present invention with a deviation pipe through which only a portion of the fluid in the main pipe flows. Similarly, it may be a sampling system in the case of a tank and in which some fluid is drawn from the tank for analysis. As for the term "fluid", it refers to any liquid, slurry, mixture, or the like that flows inside the pipe and that exhibits a power law behavior therein.

Background the Equations

When a fluid flows in a pipe, the effective shear rate (γ) is linked to the mean flow velocity (V) of the fluid by:

$$\dot{\gamma} = K_s \frac{V}{D} \tag{1}$$

where D is the diameter of the pipe and $K_S$ is a constant that depends on the geometry of the system.

In the case of a Newtonian fluid, the power correlation is written as:

$$K_P = N_P Re \tag{2}$$

where:

$$N_P = \frac{\Delta P D}{\rho V^2 L} \quad (3)$$

and:

$$Re = \frac{\rho V D}{\mu} \quad (4)$$

$K_P$ is another constant that depends on the geometry of the system, $N_P$ is the power number, Re is the Reynolds number, $\Delta P$ is the pressure drop through the pipe, L is the length of the pipe, and p is the density of the fluid.

Power law fluids are characterized by the following relation:

$$\tau = k \dot{\gamma}^n \quad (5)$$

where $\tau$ represents the stress, k is the consistency index, and n is the power law index.

Equation 2 can be generalized by the approach set forth by Riéger and Novák in 1973 for a non-Newtonian power law fluid:

$$K_{p(n)} = N_P Re_{PL} \quad (6)$$

where:

$$Re_{PL} = \frac{\rho V^{2-n} D^n}{8^{n-1} k} \quad (7)$$

$K_{p(n)}$ is a constant that depends on the geometry of the system when a power law fluid flows therein. $Re_{PL}$ is the generalized Reynolds number for a power law fluid.

Combining both the Metzner and Otto concept and an approximation of the Riéger and Novák, it follows that:

$$K_s = \left( \left[ \frac{K_{p(n)}}{K_p} \right] \right)^{\frac{1}{n-1}} \quad (8)$$

The fluid being tested flows at a mean flow velocity (V) in a pipe having a given diameter (D). The mean flow velocity (V) is expressed in terms of meters per second or the equivalent. The values of the mean flow velocity (V) and the diameter (D) are preferably those of the main pipe on which is installed an apparatus according to the present invention. The diameter (D) should remain constant throughout the path of the fluid in the apparatus in order to minimize the perturbations that might be generated in the fluid.

There are two main ways of determining the mean flow velocity (V). The first is to measure the mean flow velocity (V) with an appropriate sensor. The second is to calibrate the supply pump used to move the fluid. The supply pump is either the supply pump of the system to which the rheological apparatus is connected or either an additional pump provided therewith.

Using the mean flow velocity (V) of the fluid, one can apply the following equations:

$$n = 1 + \frac{\log\left[\frac{\Delta P_2 K_{p1} L_1}{\Delta P_1 K_{p2} L_2}\right]}{\log\left[\frac{K_{s2}}{K_{s1}}\right]} \quad (9)$$

$$k = \frac{\Delta P_1 D^{(n+1)}}{K_{p1} [8 K_{s1}]^{(n-1)} V^n L_1} \quad (10)$$

where $K_S$, $K_{P1}$ are the geometrical constants of the first static mixer, $K_{S2}$, $K_{P2}$ are the geometrical constants of the second static mixer, D is the diameter of the pipe, $L_1$ is the internal length of the first static mixer, and $L_2$ is the internal length of the second static mixer.

If desired, the apparent viscosity ($\eta$) can be calculated. This may be done for a power law fluid with the following equation:

$$\eta = k \left( K'_s \frac{V}{D} \right)^{n-1} \quad (11)$$

where $K_s'$ is the geometrical constant of a given location where the apparent viscosity (72) is to be measured. For instance, if the apparent viscosity ($\eta$) has to be calculated in the first static mixer, the value of $K_s'$ is that of $K_{S1}$. If the apparent viscosity ($\eta$) has to be calculated in a free pipe, the value of $K_s'$ is 8, which is a value known in the art.

The apparent viscosity ($\eta$) can be directly calculated by incorporating the equations 9 and 10 into equation 11. In that case, even though the actual values of the consistency index (k) and power law index (n) are not known to an outside operator when the calculations occur within a computer, they shall be considered as being calculated since they form parts of the equation of the apparent viscosity ($\eta$).

Calibration Procedure

As aforesaid, the values of the geometrical constants $K_{S1}$, $K_{P1}$, $K_{S2}$, and $K_{P2}$ are determined through a calibration procedure involving a power correlation between a Newtonian model fluid and a non-Newtonian power law model fluid. Preferably, the calibration procedure comprises the sub-steps of measuring a first set of first and second pressure differentials ($\Delta P_1'$, $\Delta P_2'$) with a Newtonian model fluid flowing at a mean flow velocity (V) and whose dynamic viscosity ($\mu$) is known. Similarly, a second set of first and second pressure differentials ($\Delta P_1''$, $\Delta P_2''$) are measured with a non-Newtonian power law model fluid flowing at a mean flow velocity (V) equal to that of the Newtonian model fluid. The non-Newtonian model fluid has a consistency index (k) and a power law index (n) which are known.

The geometrical constants $K_{S1}$, $K_{P1}$, $K_{S2}$, and $K_{P2}$ are calculated from the following formulas:

$$K_{s1} = \frac{D}{8D} * \left( \left[ \frac{\Delta P_1''}{\Delta P_1'} * \frac{\mu}{k} \right] \right)^{\left(\frac{1}{n-1}\right)} \quad (12)$$

$$K_{p1} = \frac{\Delta P_1' D^2}{\mu L_1 V} \quad (13)$$

$$K_{s2} = \frac{D}{8V} * \left( \left[ \frac{\Delta P_2''}{\Delta P_2'} * \frac{\mu}{k} \right] \right)^{\left(\frac{1}{n-1}\right)} \quad (14)$$

$$K_{p2} = \frac{\Delta P_2^2 D^2}{\mu L_2 V} \qquad (15)$$

where D is the diameter of the pipe, $L_1$ is the internal length of the first static mixer, and $L_2$ is the internal length of the second static mixer.

Advantageously, several combinations of one or several Newtonian model fluids with several non-Newtonian power law model fluids are used to improve the accuracy of the calibration. For instance, one Newtonian model fluid may be used with several non-Newtonian power law model fluids whose consistency index (k) and power law index (n) cover the range of values of measurements. A mean value of the geometrical constants $K_{S1}$, $K_{P1}$, $K_{S2}$, and $K_{P2}$ is then calculated from individual values thereof for each combination of Newtonian and non-Newtonian fluids.

All calculations are preferably achieved in a computer. The values of the constants are then recorded in the memory of the computer.

Description of the Apparatus

An apparatus (10) according to a possible and preferred embodiment of the present invention is described hereinafter and illustrated in FIGS. 1 to 4. This apparatus (10) constitutes an example of a device to achieve the method. However, the method may also be put into practice using a different apparatus.

The apparatus (10) comprises a first static mixer (12) and a second static mixer (14). Both are mounted in series and all the fluid coming from a main supply pipe (16) is passed therein. The fluid immediately returns into the main pipe (16) afterwards. The outlet of the first static mixer (12) is connected to the inlet of the second static mixer (14) by means of an intermediary pipe (18), which can be a section of the main pipe (16) itself. As aforesaid, one could also deviate only a portion of the fluid through the apparatus (10) from the main pipe (16) or simply draw fluid from a tank (not shown) for analysis.

The static mixers (12,14) are said to be non-identical because they should not create the same pressure drops in the fluid. Identical values of the pressure drops will not give good results. The highest pressure drop can be created in the first (12) or the second static mixer (14).

Many different models of static mixers are found on the market. The shape, the flow characteristics, and the internal construction differ from one model to another. A number of factors have to be considered, such as the required extent of the mix, the pressure drop in the mixer, the diameter, the length, the shear rate, the stagnation time, and the heat transfer. Most static mixers can be classified in either one of two categories. The first category includes the ones in which the mixing occurs by rotation in a tube. These static mixers are relatively long and the pressure drop therein is low. The second class comprises the static mixers in which the mixing occurs by stretching the fluid. These mixers are short and the pressure drop therein is high.

The apparatus (10) is preferably provided with static mixers of the first category. An example of a first static mixer is a Low Pressure Drop (LPD) mixer manufactured by ROSS™ and schematically illustrated in FIG. 4. Assuming that the illustrated static mixer is the first static mixer (12), the static mixer (12) comprises a main vessel (26) and sets of two semi-elliptical baffles (28) intersecting each other with an angle, typically having a value of 45° or 60° with reference to the flow therein. Other models of static mixers may be used.

There are many considerations to be taken into account when designing a rheological apparatus. For instance, the apparatus should not have a region where the fluid becomes stagnant or where solids may accumulate. Then, the flow has to be laminar, i.e. substantially non-turbulent, and with the minimum of perturbations since they decrease the precision of the apparatus and method. As aforesaid, the diameter of the main pipe (16), the static mixers (12,14), and the intermediary pipe (18) should be the same. Yet, the section of the main pipe (16) should be long enough between a supply pump, if any, and the inlet of the first static mixer (12). The same comment applies to the outlet of the first static mixer (12) and the inlet of the second static mixer (14). However, the pipes should not be too long for preventing sedimentation to occur. Other arrangements (not shown) may be used to lower the perturbations in the flow, if necessary. Sufficient time should also be given for the flow to stabilize whenever the flow rate changes.

The pressure drops through each static mixer (12, 14) are expressed as pressure differentials using appropriate sensors or any other suitable means. Differential pressure sensors are preferred over direct pressure measurements and subsequent subtraction of the measured values, since typically, the pressure loss can be as low as 100 Pa with a line pressure between 100 and 300 kPa. FIGS. 2 and 3 show an example of an arrangement used to achieve this goal. In this arrangement, three highly sensitive measuring cells are used, namely a first cell (20), a second cell (22), and a third cell (24). The first cell (20) is mounted on the apparatus (10) upstream of the inlet of the first static mixer (12); the second cell (22) is mounted on the intermediary pipe (18), near the inlet of the second static mixer (14); and the third cell (24) is mounted downstream of the outlet of the second static mixer (14). These cells (20, 22, 24) are connected in pairs by means of a circuit of rigid tubes (30, 32, 34, 36) leading to corresponding differential pressure transducers (40, 42). The first cell (20) is connected to a first side of the first differential pressure transducer (40) by means of the first tube (30). The second cell (22) is connected to a second side of the first differential pressure transducer (40) by means of the second (32) and the third tube (34). The second cell (22) is also connected to a first side of the second differential pressure transducer (42) by means of the second (32) and the third tube (34). The third cell (24) is connected to a second side of the second differential pressure transducer (42).

The tubes (30, 32, 34, 36) are filled with a substantially incompressible liquid, such as water or ethylene glycol. Each cell (20,22,24) comprises a deformable membrane (25) made of material that is able to correctly transmit the pressure to the incompressible liquid and resist the abrasion of the fluid. Natural or synthetic rubber are examples of materials for the membrane (25). A purge opening (60) is provided to drain any air out of the tubes (30, 32, 34, 36). Air is also drained out through a small opening (62) located against the internal membrane of a transducer, such as the first transducer (40). The tubes (30, 32, 34, 36) are filled through a valve (64).

The pressure drop of the fluid through the first static mixer (12) is measured by the first differential pressure transducer (40) and the pressure drop of the fluid through the second static mixer (14) is measured by the second differential pressure transducer (42). Each transducer (40, 42) comprises an output terminal by which a corresponding differential pressure signal $\Delta P_1$, or $\Delta P_2$ is sent. The terminals are connected to a computer (50) by electrical wires (52, 54) or any other suitable arrangements. The computer (50) preferably performs all calculations in corresponding subroutines including the formulas described hereinabove.

The present invention may be used to measure the rheological properties of fluids in a wide range of applications, such as paper manufacturing or coating, cosmetic or food preparation, and in polymer synthesis.

The present invention is not limited to the described embodiment and encompasses any alternative embodiments within the limits defined by the claims.

What is claimed is:

1. A method for determining the consistency index (k) and the power law index (n) of a fluid exhibiting a power law behavior when flowing through a pipe having an internal diameter (D), the fluid flowing in the pipe with a mean flow velocity (V), the method comprising the steps of:

passing the fluid in a first and a second static mixer through which the fluid flows in a laminar manner, the first and the second static mixer being in fluid communication with each other and being non-identical, the first static mixer having predetermined geometrical constants $K_{S1}$ and $K_{P1}$ and the second static mixer having predetermined geometrical constants $K_{S2}$ and $K_{P2}$;

measuring a first pressure differential ($\Delta P_1$) corresponding to a pressure drop of the fluid through the first static mixer;

measuring a second pressure differential ($\Delta P_2$) corresponding to a pressure drop of the fluid through the second static mixer; and calculating the consistency index (k) and the power law index (n) using the first and second pressure differentials ($\Delta P_1$, $\Delta P_2$), the mean flow velocity (V), and the geometrical constants $K_{S1}$, $K_{P1}$, $K_{S2}$, and $K_{P2}$ according to an approximation of Metzner and Otto concept generalized to static mixers.

2. A method according to claim 1, wherein the step of calculating the consistency index (k) and the power law index (n) uses the following formulas:

$$n = 1 + \frac{\log\left[\frac{\Delta P_2 K_{p1} L_1}{\Delta P_1 K_{p2} L_2}\right]}{\log\left[\frac{K_{s2}}{K_{s1}}\right]}$$

$$k = \frac{\Delta P_1 D^{(n+1)}}{K_{p1}[8K_{s1}]^{(n-1)} V^n L_1}$$

where $L_1$ is the internal length of the first static mixer and $L_2$ is the internal length of the second static mixer.

3. A method according to claim 2, further comprising the step of measuring the mean flow velocity (V) of the fluid.

4. A method according to claim 2, further comprising the step of calculating the apparent viscosity ($\eta$) of the fluid using the consistency index (k) and the power law index (n).

5. A method according to claim 4, wherein the step of calculating the apparent viscosity ($\eta$) involves the following formula:

$$\eta = \left(k\left(K_s'\frac{V}{D}\right)\right)^{n-1}$$

where $K_s'$ is the geometrical constant of a given location where the apparent viscosity ($\eta$) is to be measured.

6. A method according to claim 1, wherein the step of calculating the consistency index (k) and the power law index (n) is achieved by a computer.

7. A method according to claim 6, wherein the steps of measuring the first and the second pressure differentials ($\Delta P_1$, $\Delta_{P2}$), and the step of calculating the consistency index (k) and the power law index (n), are carried out repetitively to provide a continuous monitoring of the fluid.

8. A method according claim 1, further comprising the initial step of determining the values of the geometrical constants $K_{S1}$, $K_{P1}$, $K_{S2}$, and $K_{P2}$ through a calibration procedure.

9. A method according to claim 8, wherein the calibration procedure comprises the sub-steps of:

passing a laminar flow of a Newtonian model fluid in the first and the second static mixer, the Newtonian model fluid flowing at a mean flow velocity (V) and having a known dynamic viscosity ($\Phi$);

measuring a first set of first and second pressure differentials ($\Delta P_1'$, $\Delta P_2'$) corresponding to a pressure drop of the Newtonian model fluid through the first and second static mixer, respectively;

passing a laminar flow of a non-Newtonian power law model fluid in the first and the second static mixer, the non-Newtonian power law model fluid flowing at a mean flow velocity (V) equal to that of the Newtonian model fluid and having a known consistency index (k) and power law index (n);

measuring a second set of first and second pressure differentials ($\Delta P_1''$, $\Delta P_2''$) corresponding to a pressure drop of the non-Newtonian power law model fluid through the first and second static mixer, respectively; and calculating the geometrical constants $K_{S1}$, $K_{P1}$, $K_{S2}$, and $K_{P2}$ from the following formulas;

$$K_{s1} = \frac{D}{8V} * \left[\frac{\Delta P_1''}{\Delta P_1'} * \frac{\mu}{k}\right]^{\left(\frac{1}{n-1}\right)}$$

$$K_{p1} = \frac{\Delta P_1' D^2}{\mu L_1 V}$$

$$K_{s2} = \frac{D}{8V} * \left[\frac{\Delta P_2''}{\Delta P_2'} * \frac{\mu}{k}\right]^{\left(\frac{1}{n-1}\right)}$$

$$K_{p2} = \frac{\Delta P_2' D^2}{\mu L_2 V}$$

where D is the diameter of the pipe, $L_1$ is the internal length of the first static mixer, and $L_2$ is the internal length of the second static mixer.

10. A method according to claim 9, wherein several combinations of Newtonian and non-Newtonian power law model fluids are used, the method further comprising the sub-step of calculating a mean value of the geometrical constants $K_{S1}$, $K_{P1}$, $K_{S2}$, and $K_{P2}$ from individual values thereof for each combination of Newtonian and non-Newtonian fluids.

11. An apparatus for measuring the consistency index (k) and the power law index (n) of a fluid exhibiting a power law behavior when flowing through a pipe having a given diameter (D) and with a mean flow velocity (V), the apparatus comprising:

a first static mixer having an inlet and an outlet, the inlet of the first static mixer being connected to the pipe, the first static mixer having predetermined geometrical constants $K_{S1}$ and $K_{P1}$;

a second static mixer having an inlet, an outlet, and being non-identical to the first static mixer, the outlet of the second static mixer being connected to the pipe, the second static mixer having predetermined geometrical constants $K_{S2}$ and $K_{P2}$;

an intermediary pipe connected between the outlet of the first static mixer and the inlet of the second static mixer;

first means for measuring a first pressure differential ($\Delta P_1$) corresponding to a pressure drop of a laminar flow of the fluid through the first static mixer;

second means for measuring a second pressure differential ($\Delta P_2$) corresponding to a pressure drop of the laminar flow of fluid through the second static mixer; and means for calculating the consistency index (k) and the power law index (n) according to an approximation of Metzner and Otto concept generalized to static mixers.

12. An apparatus according to claim 11, wherein the Metzner and Otto concept generalized to static mixers uses the following formulas:

$$n = 1 + \frac{\log\left[\frac{\Delta P_2 K_{pl} L_1}{\Delta P_1 K_{p2} L_2}\right]}{\log\left[\frac{K_{s2}}{K_{sl}}\right]}$$

$$k = \frac{\Delta P_1 D^{(n+1)}}{K_{pl}[8K_{sl}]^{(n-1)} V^n L_1}$$

where $L_1$ is the total internal length of the first static mixer and $L_2$ is the total internal length of the second static mixer.

13. An apparatus according to claim 12, further comprising fourth means for measuring the mean flow velocity (V) of the fluid.

14. An apparatus according to claim 12, further comprising means for calculating the apparent viscosity ($\eta$) of the fluid.

15. An apparatus according to claim 14, wherein the means for calculating the apparent viscosity ($\eta$) involves the following formula:

$$\eta = k\left(K'_s \frac{V}{D}\right)^{n-1}$$

where $K_s'$ is the geometrical constant of a given location where the apparent viscosity ($\eta$) is to be measured.

16. An apparatus according to claim 11, further comprising means for calculating the geometrical constants $K_{S1}$, $K_{P1}$, $K_{S2}$, and $K_{P2}$ through a calibration procedure.

17. An apparatus according to claim 16, wherein the means for calculating the geometrical constants $K_{S1}$, $K_{P1}$, $K_{S2}$, and $K_{P2}$ comprises:

means for measuring a first set of first and second pressure differentials ($\Delta P_1'$, $\Delta P_2'$) with a Newtonian model fluid flowing in a laminar manner at a mean flow velocity (V) and whose dynamic viscosity ($\Phi$) is known;

means for measuring a second set of first and second pressure differentials ($\Delta P_1''$, $\Delta P_2''$) with a non-Newtonian power law model fluid flowing in a laminar manner at a mean flow velocity (v) equal to that of the Newtonian model fluid, the non-Newtonian model fluid having a consistency index (k) and the power law index (n) which are known; and means for calculating the geometrical constants $K_{S1}$, $K_{P1}$, $K_{S2}$, and $K_{P2}$ from the following formulas:

$$K_{sl} = \frac{D}{8V} * \left[\frac{\Delta P_1''}{\Delta P_1'} * \frac{\mu}{k}\right]^{\left(\frac{1}{n-1}\right)}$$

$$K_{pl} = \frac{\Delta P_1' D^2}{\mu L_1 V}$$

$$K_{s2} = \frac{D}{8V} * \left[\frac{\Delta P_2''}{\Delta P_2'} * \frac{\mu}{k}\right]^{\left(\frac{1}{n-1}\right)}$$

$$K_{p2} = \frac{\Delta P_2' D^2}{\mu L_2 V}$$

where D is the diameter of the pipe, $L_1$ is the internal length of the first static mixer, and $L_2$ is the internal length of the second static mixer.

18. An apparatus for measuring the consistency index (k) and the power law index (n) of a fluid exhibiting a power law behavior when flowing through a pipe, the apparatus comprising:

a first static mixer having an inlet and an outlet, the inlet of the first static mixer being connected to the pipe, the first static mixer having predetermined geometrical constants $K_{S1}$ and $K_{P1}$;

a second static mixer having an inlet and an outlet, the outlet of the second static mixer being connected to the pipe, the second static mixer having predetermined geometrical constants $K_{S2}$ and $K_{P2}$, where $K_{S2}$ is non-identical to $K_{S1}$;

an intermediary pipe mounted between the outlet of the first static mixer and the inlet of the second static mixer;

a first pressure cell mounted on the pipe before the inlet of the first static mixer;

a second pressure cell mounted on the intermediary pipe;

a third pressure cell mounted on the pipe after the outlet of the second static mixer;

a first differential pressure transducer connected between the first and the second pressure cell, the first differential pressure transducer having an output terminal for a first pressure differential signal ($\Delta P_1$) indicative of a pressure drop of the fluid through the first static mixer;

a second differential pressure transducer connected between the second and the third pressure cell, the second differential pressure transducer having an output terminal for a second pressure differential signal ($\Delta P_2$) indicative of a pressure drop of the fluid through the second static mixer; and a computer having a subroutine in which the consistency index (k) and the power law index (n) are calculated according to an approximation of Metzner and Otto concept generalized to static mixers.

19. An apparatus according to claim 18, wherein the Metzner and Otto concept generalized to static mixers uses the following formulas:

$$n = 1 + \frac{\log\left[\frac{\Delta P_2 K_{pl} L_1}{\Delta P_1 K_{p2} L_2}\right]}{\log\left[\frac{K_{s2}}{K_{sl}}\right]}$$

$$k = \frac{\Delta P_1 D^{(n+1)}}{K_{pl}[8K_{sl}]^{(n-1)} V^n L_1}$$

where D is the diameter of the pipe, $L_1$ is the total internal length of the first static mixer, and $L_2$ is the total internal length of the second static mixer.

20. An apparatus according to claim 19, further comprising a mean flow velocity sensor connected to the computer.

21. An apparatus according to claim 20, wherein the computer comprises a subroutine to calculate a value indicative of the apparent viscosity ($\eta$).

22. An apparatus according to claim 21, wherein the subroutine comprises the following formula:

$$\eta = k\left(K'_s \frac{V}{D}\right)^{n-1}$$

where $K_s'$ is the geometrical constant of a given location where the apparent viscosity ($\eta$) is to be measured.

* * * * *